US00PP13140P2

(12) United States Plant Patent
Oliver

(10) Patent No.: US PP13,140 P2
(45) Date of Patent: Oct. 29, 2002

(54) HEUCHERA PLANT NAMED 'ROSE MIRRORS'

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 10/014,461

(22) Filed: Dec. 8, 2001

(51) Int. Cl.[7] ..... A01H 5/00
(52) U.S. Cl. ..... Plt./263
(58) Field of Search ..... Plt./263

(56) References Cited

U.S. PATENT DOCUMENTS

PP8,984 P * 11/1994 Heims ..... Plt./263
PP11,059 P * 9/1999 Oliver ..... Plt./263
PP11,111 P * 10/1999 Oliver ..... Plt./263

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Heuchera plant named 'Rose Mirrors', characterized by its full and uniformly mounded plant habit; silvery gray and red purple-colored upper leaf surfaces; dark red purple-colored lower leaf surfaces; numerous showy pink-colored flowers arranged on erect to slightly outwardly spreading panicles; and excellent garden performance.

1 Drawing Sheet

BOTANICAL CLASSIFICATION/CULTIVAR DESIGNATION

*Heuchera sp.* cultivar Rose Mirrors.

BACKGROUND OF THE INVENTION

The present invention relates to a new and distinct cultivar of Heuchera plant, botanically known as *Heuchera sp.* and hereinafter referred to by the name 'Rose Mirrors'.

The new Heuchera is a product of a planned breeding program conducted by the Inventor in Scottdale, Pa. The objective of the breeding program is to create new Heuchera cultivars having good plant vigor, dense and uniform plant habit, and showy and attractive flower and leaf coloration.

The new Heuchera was discovered by the Inventor in a controlled environment in Scottdale, Pa., from seedling progeny from a cross-pollination made by the Inventor in May, 1996, of the Heuchera cultivar Petite Marbled Burgundy, disclosed in U.S. Plant Pat. No. 11,059, as the female, or seed, parent with the Heuchera cultivar Harmonic Convergence, disclosed in U.S. Plant Pat. No. 11,111, as the male, or pollen, parent. The new Heuchera was selected by the Inventor in May, 1997. The selection of this plant was based on its desirable flower and foliage coloration.

Asexual reproduction of the new Heuchera by cuttings taken in a controlled environment in Scottdale, Pa., since August, 1997, has shown that the unique features of this new Heuchera are stable and reproduced true to type in successive generations.

SUMMARY OF THE INVENTION

The cultivar Rose Mirrors has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Rose Mirrors'. These characteristics in combination distinguish 'Rose Mirrors' as a new and distinct cultivar:

1. Full and densely foliated; uniformly mounded plant habit.
2. Upper leaf surfaces silvery gray in color with contrasting red purple venation; lower leaf surfaces dark red purple in color.
3. Numerous showy pink-colored flowers arranged on erect to slightly outwardly spreading panicles.
4. Excellent garden performance.

Plants of the new Heuchera can be compared to plants of the female parent, the cultivar Petite Marbled Burgundy. In side-by-side comparisons conducted by the Inventor in Scottdale, Pa., plants of the new Heuchera differed from plants of the cultivar Petite Marbled Burgundy in the following characteristics:

1. Plants of the new Heuchera were larger than plants of the cultivar Petite Marbled Burgundy.
2. Plants of the new Heuchera had larger leaves than plants of the cultivar Petite Marbled Burgundy.
3. Upper leaf surfaces of plants of the new Heuchera were silvery gray with red purple venation whereas upper leaf surfaces of plants of the cultivar Petite Marbled Burgundy were marbled with silvery gray patches extending to the leaf margins.
4. Plants of the new Heuchera had much longer flowering stems than plants of the cultivar Petite Marbled Burgundy.
5. Sepal color of plants of the new Heuchera was darker pink than sepal color of plants of the cultivar Petite Marbled Burgundy.

Plants of the new Heuchera can be compared to plants of the male parent, the cultivar Harmonic Convergence. In side-by-side comparisons conducted by the Inventor in Scottdale, Pa., plants of the new Heuchera differed from plants of the cultivar Harmonic Convergence in the following characteristics:

1. Upper leaf surfaces of plants of the new Heuchera had smaller areas of silvery gray than upper leaf surfaces of plants of the cultivar Harmonic Convergence.
2. Panicles of plants of the new Heuchera were not basally branching whereas panicles of plants of the cultivar Harmonic Convergence were basally branching.
3. Petals of plants of the new Heuchera were not recurved whereas petals of plants of the cultivar Harmonic Convergence were recurved.

Plants of the new Heuchera can be compared to plants of the cultivar Silver Scrolls, disclosed in U.S. Plant Pat. No. 12,066. In side-by-side comparisons conducted by the Inventor in Scottdale, Pa., plants of the new Heuchera differed from plants of the cultivar Silver Scrolls in the following characteristics:

1. Plants of the new Heuchera had shorter flowering stems than plants of the cultivar Silver Scrolls.
2. Plants of the new Heuchera had pink-colored flowers whereas plants of the cultiver Silver Scrolls had white-colored flowers.
3. Flowering stems of plants of the new Heuchera were not as erect as flowering stems of plants of the cultivar Silver Scrolls.

Plants of the new Heuchera can also be compared to plants of the cultivar Pewter Veil, disclosed in U.S. Plant Pat. No. 8,984. In side-by-side comparisons conducted by the Inventor in Scottdale, Pa., plants of the new Heuchera differed from plants of the cultivar Pewter Veil in the following characteristics:

1. Plants of the new Heuchera had smaller leaves than plants of the cultivar Pewter Veil.
2. Upper leaf surfaces of plants of the new Heuchera were silvery gray in color with contrasting red purple venation whereas upper leaf surfaces of plants of the cultivar Pewter Veil were gray green suffused with purple coloration.
3. Leaf surfaces of plants of the new Heuchera were smooth whereas leaf surfaces of plants of the cultivar Pewter Veil were rugose.
4. Plants of the new Heuchera had shorter flowering stems than plants of the cultivar Pewter Veil.
5. Plants of the new Heuchera had showy pink-colored flowers whereas plants of the cultivar Pewter Veil had non-showy yellow green-colored flowers.

BRIEF DESCRIPTION OF THE PHOTOGRAPH

The accompanying colored photograph illustrates the overall appearance of the new Heuchera, showing the colors as true as it is reasonably possible to obtain in colored reproductions of this type. Colors in the photograph may differ slightly from the color values cited in the detailed botanical description which accurately describe the colors of the new Heuchera. The photograph comprises a side perspective view of a typical flowering plant of 'Rose Mirrors'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Keller, Tex. during the summer in an unshaded outdoor nursery and under cultural conditions which approximate commercial practice. Plants were grown as single plants in one-gallon containers and were about two years old. Measurements and numerical values represent averages taken from a group of flowering plants.

Botanical classification: *Heuchera sp.* cultivar Rose Mirrors.

Parentage:

*Female, or seed, parent.*—*Heuchera sp.* cultivar Petite Marbled Burgundy, disclosed in U.S. Plant Pat. No. 11,059.

*Male, or pollen, parent.*—*Heuchera sp.* cultivar Harmonic Convergence, disclosed in U.S. Plant Pat. No. 11,111.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous and well-branched.

Plant description:

*Appearance.*—Perennial; basal rosette plant habit with leaves developing from the base; densely foliated; full, mounded and uniform plant habit with upright to slightly outwardly angled panicles with showy pink-colored flowers. Vigorous and robust growth habit.

*Plant size.*—Height: Soil level to top of foliar plane: About 20 cm. Soil level to top of panicles: About 53 cm. Diameter or spread: About 47 cm.

*Foliage description.*—Arrangement: Basal rosette, simple. Length: About 8.6 cm. Width: About 8.3 cm. Shape: Cordate. Apex: Mostly rounded and mucronate. Base: Cordate. Margin: Crenate and serrulate with fine ciliation. Texture, upper and lower surfaces: Smooth, glabrous. Venation pattern: Palmate, reticulate. Color: Developing and fully expanded leaves, upper surface: Darker than 198A with 187A and 79A overtones. Developing and fully expanded leaves, lower surface: Closest to, but more red purple than 79A or darker than 187A. Venation: Upper surface: Close to 200A with 187A and 79A overtones. Lower surface: Closest to, but more red purple than 79A or darker than 187A. Petiole: Length: About 17 cm. Diameter: About 2.5 mm. Texture, upper and lower surfaces: Smooth, glabrous. Color, upper and lower surfaces: Close to 187A.

Flower description:

*Appearance/arrangement.*—Single campanulate flowers arranged on numerous erect to slightly outwardly spreading panicles; about 87 flowers and flower buds per flowering stem. Flowers face outward to slightly upright. Flowering continuous with at least eight flowering stems per plant developing throughout the flowering period. Flowers persistent. Flowers not fragrant.

*Time of flowering.*—Under natural conditions, plants flower in the late spring and early summer.

*Inflorescence longevity.*—Individual inflorescences last about one week on the plant.

*Inflorescence size.*—Length: About 53 cm. Diameter: About 4.5 cm.

*Flower size.*—Diameter: About 5 mm. Depth (height): About 6 mm.

*Flower buds.*—Height: About 2 mm. Diameter: About 2 mm. Shape: Spherical. Color, at stage of showing color: 71A.

*Sepals.*—Quantity/arrangement: Five sepals; radially symmetrical and fused at base. Length: About 5.5 mm. Width: About 2 mm. Shape: Elongate. Apex: Acute. Margin: Entire. Texture: Pubescent. Color: When opening and fully opened, upper and lower surfaces: Pink; white, close to 155D, ground color overlain with dark pink, 71A, minute spots.

*Petals.*—Quantity/arrangement: Five minute petals; radially symmetrical and fused at base. Length: About 4 mm. Width: About 1 mm. Shape: Narrowly spatulate. Apex: Acute. Margin: Entire. Texture: Smooth, glabrous. Color: When opening, upper and lower surfaces: 71A. Fully opened, upper and lower surfaces: Pink; white ground color, close to 155D, overlain with dark pink, 71A, minute spots.

*Peduncle.*—Strength: Moderately strong; flexible. Aspect: Mostly upright to slightly angled outwardly to 20° from vertical. Length: About 51 cm. Diameter: About 2 mm. Texture: Smooth. Color: Close to 148A overlain with 187A.

*Pedicels.*—Strength: Moderately strong; wiry. Aspect: About 40 to 45° from vertical. Length: About 2.7 cm. Diameter: Less than 1 mm. Texture: Pubescent. Color: Close to 148A overlain with 187A.

*Reproductive organs.*—Androecium: Stamen number: Five per flower. Anther shape: Bi-lobed. Anther length: Less than 1 mm. Anther color: Close to 17A. Amount of pollen: Scarce. Pollen color: Close to 7A. Gynoecium: Pistil number: One per flower. Pistil length: About 5.5 mm. Stigma shape: Forked, linear. Stigma color: 155D. Style color: 155D. Ovary color: 155D.

*Seed/fruit.*—Seed and/or fruit production has not been observed.

Disease/pest resistance: Resistance to pathogens and pests common to Heuchera has not been observed on plants grown under commercial conditions.

Temperature tolerance: Plants of the new Heuchera have demonstrated good tolerance to night temperatures as low as −35° C. and day temperatures as high as 45° C.

It is claimed:

1. A new and distinct cultivar of Heuchera plant named 'Rose Mirrors', as illustrated and described.

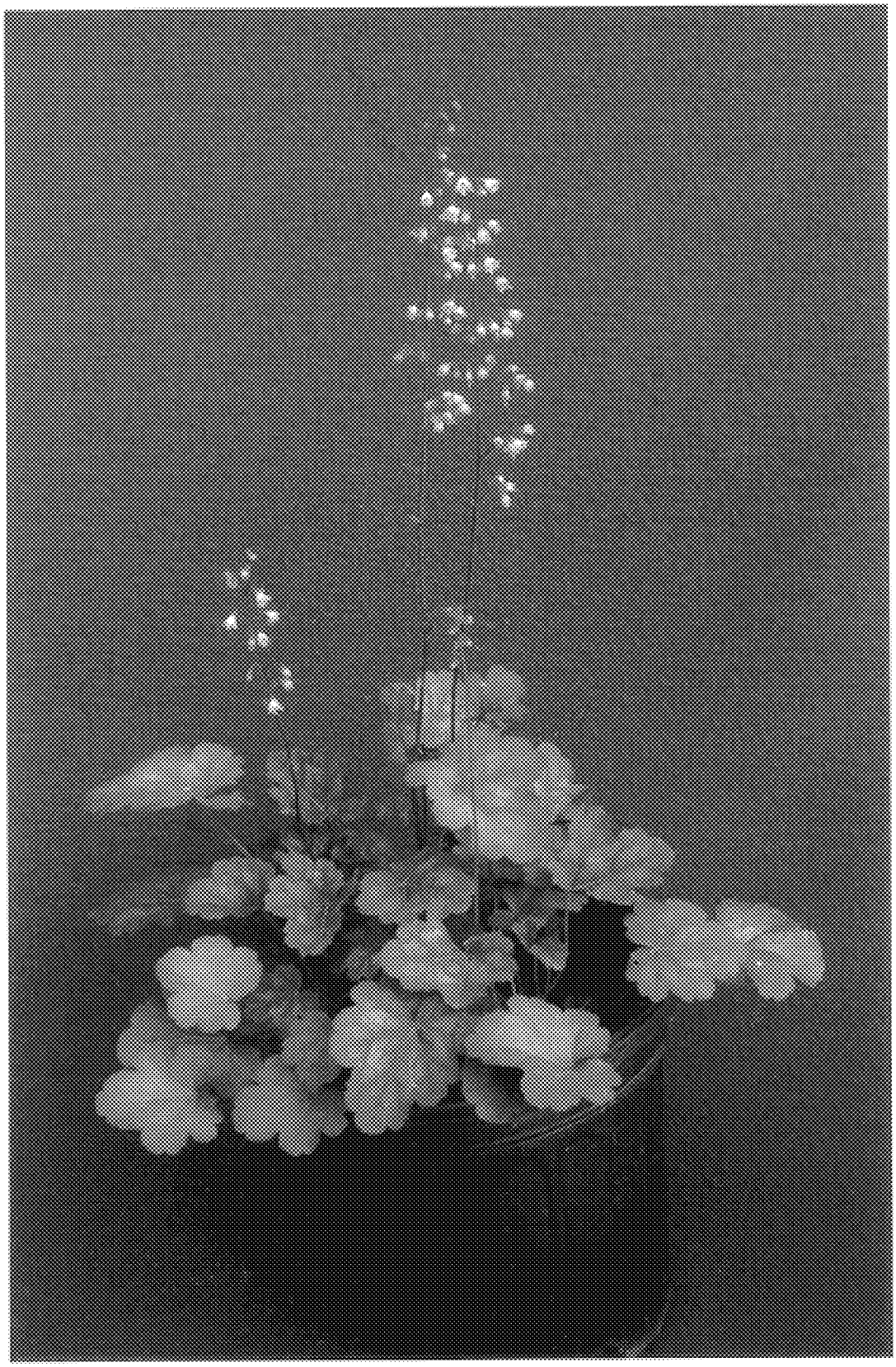

* * * * *